United States Patent
Rezach et al.

(10) Patent No.: US 11,083,598 B2
(45) Date of Patent: Aug. 10, 2021

(54) SPINAL IMPLANT AND METHOD OF USE

(71) Applicant: Warsaw Orthopedic, Inc., Warsaw, IN (US)

(72) Inventors: William Alan Rezach, Covington, TN (US); Jason M. May, St. Johns, FL (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 15 days.

(21) Appl. No.: 16/380,754

(22) Filed: Apr. 10, 2019

(65) Prior Publication Data

US 2020/0323651 A1    Oct. 15, 2020

(51) Int. Cl.
| | |
|---|---|
| *A61F 2/46* | (2006.01) |
| *A61F 2/44* | (2006.01) |
| *A61F 2/30* | (2006.01) |
| *A61F 2/00* | (2006.01) |

(52) U.S. Cl.
CPC ............ *A61F 2/4611* (2013.01); *A61F 2/442* (2013.01); *A61F 2/30744* (2013.01); *A61F 2/4455* (2013.01); *A61F 2220/0025* (2013.01)

(58) Field of Classification Search
CPC . A61B 17/70; A61B 17/7001; A61B 17/7082; A61B 17/7035; A61B 17/7037; A61B 17/7038; A61B 17/704; A61B 17/7046; A61B 17/8605; A61B 17/8665
See application file for complete search history.

(56) References Cited

U.S. PATENT DOCUMENTS

| | | | |
|---|---|---|---|
| 5,019,079 | A | 5/1991 | Ross |
| D411,009 | S | 6/1999 | Asfora |
| 6,726,689 | B2 | 4/2004 | Jackson |
| 7,044,953 | B2 | 5/2006 | Capanni |
| 8,628,581 | B2 | 1/2014 | Zang |
| 9,161,745 | B2 | 10/2015 | Dodson |
| 9,295,488 | B2 | 3/2016 | Asfora |
| 9,561,055 | B1 | 2/2017 | Karim |
| 10,085,776 | B2 | 10/2018 | Blain |
| D834,194 | S | 11/2018 | Blain et al. |

(Continued)

OTHER PUBLICATIONS

International Search Report and the Written Opinion of the International Searching Authority—PCT/US2019/056672, dated Feb. 6, 2020—ISA/KR, International Application Division,Korean Intellectual Property Office, 189 Cheongsa-ro, Seo-gu, Dageon, 35208, Republic of Korea.

*Primary Examiner* — Matthew J Lawson
*Assistant Examiner* — Lisa Nguyen
(74) *Attorney, Agent, or Firm* — Sorell, Lenna & Schmidt, LLP

(57) ABSTRACT

A surgical coupling member includes a shaft defining an axis and including at least one thread having an external thread form. The external thread form having a leading flank and a trailing flank. The external thread form defines a pitch and a crest, the crest having a width in a range of about 35% to about 50% of the pitch of the external thread form, wherein the leading flank and the trailing flank are angled in a proximal orientation relative to the thread axis, and wherein the external thread form is configured to interlock with an internal thread form of an implant receiver. Systems, spinal constructs, implants and methods of use are disclosed.

19 Claims, 6 Drawing Sheets

(56) References Cited

U.S. PATENT DOCUMENTS

| | | |
|---|---|---|
| 10,188,429 B2 | 1/2019 | Carlson et al. |
| 10,307,185 B2 | 6/2019 | Schafer et al. |
| 2003/0045881 A1 | 3/2003 | Barouk et al. |
| 2004/0044345 A1 | 3/2004 | DeMoss et al. |
| 2006/0004378 A1* | 1/2006 | Raines, Jr. ............ A61F 2/4202 606/99 |
| 2008/0177331 A1 | 7/2008 | Perez-Cruet et al. |
| 2008/0221583 A1 | 9/2008 | Sharifi-Mehr et al. |
| 2009/0018589 A1 | 1/2009 | Smisson, III et al. |
| 2009/0306720 A1 | 12/2009 | Doubler et al. |
| 2011/0066191 A1* | 3/2011 | Jackson ............ A61B 17/7032 606/302 |
| 2011/0071572 A1* | 3/2011 | Sixto ............ A61B 17/888 606/286 |
| 2011/0218580 A1 | 9/2011 | Schwager et al. |
| 2011/0245875 A1 | 10/2011 | Karim |
| 2011/0282400 A1 | 11/2011 | Jackson |
| 2012/0071927 A1 | 3/2012 | Beger et al. |
| 2012/0172935 A1 | 7/2012 | Willert et al. |
| 2013/0218213 A1 | 8/2013 | Lemoine |
| 2014/0214084 A1 | 7/2014 | Jackson et al. |
| 2015/0265316 A1 | 9/2015 | Schwab |
| 2015/0289906 A1 | 10/2015 | Murray et al. |
| 2015/0313658 A1 | 11/2015 | Kolb |
| 2016/0038188 A1* | 2/2016 | Jackson ............ A61B 17/7035 606/267 |
| 2016/0157908 A1 | 6/2016 | Cawley et al. |

* cited by examiner

SPINAL IMPLANT AND METHOD OF USE

TECHNICAL FIELD

The present disclosure generally relates to medical devices for the treatment of spinal disorders, and more particularly to a spinal implant system including a bone fastener and a method for treating a spine.

BACKGROUND

Spinal pathologies and disorders such as scoliosis, kyphosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, the plates, connectors and/or rods may be attached via the fasteners to the exterior of one or more vertebral members. This disclosure describes an improvement over these prior technologies.

SUMMARY

In one embodiment, a surgical coupling member is provided. The coupling member includes a shaft defining an axis and including at least one thread having an external thread form. The external thread form having a leading flank and a trailing flank. The external thread form defines a pitch and a crest, the crest having a width in a range of about 35% to about 50% of the pitch of the external thread form, wherein the leading flank and the trailing flank are angled in a proximal orientation relative to the thread axis, and wherein the external thread form is configured to interlock with an internal thread form of an implant receiver. The external thread form defines a crest having a width in a range of about 35-50% of a pitch of the external thread form. The leading flank and the trailing flank are angled in a proximal orientation relative to the thread axis. The external thread form being configured to interlock with an internal thread form of an implant receiver. In some embodiments, systems, spinal constructs, implants and methods are disclosed.

In one embodiment, a spinal implant is provided. The spinal implant includes an implant receiver having at least one thread defining an internal thread form having at least one rounded corner. A coupling member includes at least one thread defining a thread axis, and an external thread form having a leading flank and a trailing flank. The leading flank and the trailing flank are angled in a proximal orientation relative to the thread axis, the external thread form defines a crest having a width in a range of about 35-50% of a pitch of the external thread form. The leading flank is disposed at a first angle relative to a transverse axis of the at least one thread and the trailing flank being disposed at a second angle relative to the transverse axis. The first angle being greater than the second angle. The external thread form is configured to interlock with the internal thread form.

In one embodiment, a spinal implant system is provided. The spinal implant system comprises at least one bone screw having an implant receiver and a tissue penetrating shaft. The implant receiver includes at least one thread defining an internal thread form having at least one rounded corner. A set screw includes at least one thread defining a thread axis, and an external thread form having a leading flank and a trailing flank. The leading flank and the trailing flank are angled in a proximal orientation relative to the thread axis. The external thread form defines a crest having a width in a range of about 35-50% of a pitch of the external thread form. The leading flank is disposed at a first angle relative to a transverse axis of the at least one thread and the trailing flank being disposed at a second angle relative to the transverse axis. The first angle is greater than the second angle. The external thread form being configured to interlock with the internal thread form. A spinal rod configured for disposal with the implant receiver and engagement with the set screw.

BRIEF DESCRIPTION OF THE DRAWINGS

The present disclosure will become more readily apparent from the specific description accompanied by the following drawings, in which.

DETAILED DESCRIPTION

Figure 1:
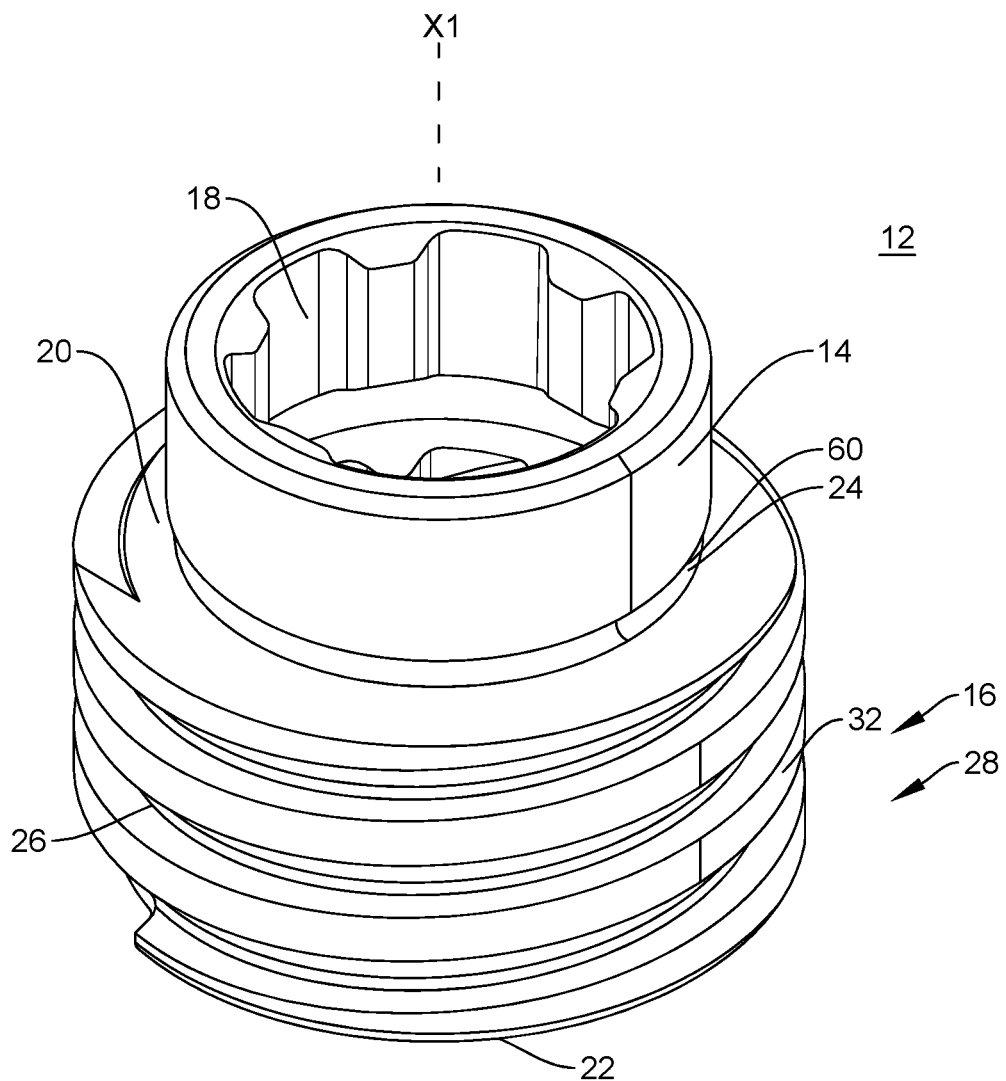
FIG. 1 is a perspective view of components of one embodiment of a surgical system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener and a method for treating a spine.

In some embodiments, the present spinal implant system includes a spinal implant, such as, for example, a bone fastener having a receiver and a set screw. In some embodiments, the set screw is configured to facilitate engagement of the set screw with the receiver. In some embodiments, the set screw is configured to contact a receiver and interlock with the receiver to reduce splay of the receiver.

In some embodiments, the set screw includes a thread form having a crest. In some embodiments, the crest includes a selected thickness. In some embodiments, the thickness includes a percentage of the thread pitch. In some embodiments, the thickness of the crest is about 45 percent of the thread pitch. In some embodiments, the thickness at the crest is configured to provide an increase in strength of the setscrew or mating receiver. In some embodiments, the present surgical system includes a set screw configured to tolerate an increased load capacity. The set screw is configured to resist and/or prevent splaying of the arms of the receiver that may occur from excessive loading. In some embodiments, splaying is due to the set screw shifting off axis within the receiver resulting in overloading of the threads due to a decreased thread contact and thinning crest width. In some embodiments, the angles of the trailing flank and the leading flank are disposed in a proximal orientation relative to a thread axis. In some embodiments, the thread geometry provides for a thicker crest width on the minor diameter of the tulip head and the major diameter of the set screw. In some embodiments, an increase in crest width facilitates resisting and/or preventing shear forces produced by a clamping force generated during engagement of the set screw with the receiver. In some embodiments, the set screw is configured to matingly engage the receiver.

In some embodiments, the receiver includes an internal thread having smooth rounded corners configured to eliminate binding and/or cutting into the set screw. In some embodiments, during engagement of the set screw with the receiver, the rounded corners become load bearing surfaces. In some embodiments, the arcuate configuration of the corners resist and/or prevent the corners from cutting into the setscrew. In some embodiments, this configuration is beneficial when the receiver includes a harder material than the set screw.

In some embodiments, the thread includes a leading edge and a trailing edge. In some embodiments, the angles of leading edge and the trailing edge form the selected thickness of the crest. In some embodiments, the leading edge is disposed at an angle greater than the angle of the trailing edge. In some embodiments, the angle of the leading edge is about 20 degrees greater than the angle of the trailing edge.

In some embodiments, leading edge is disposed at an angle relative to a transverse axis. In some embodiments, the leading edge angle is about 15 degrees relative to the transverse axis. In some embodiments, the trailing edge is disposed at an angle relative to the transverse axis. In some embodiments, the trailing edge angle is about −5 degrees relative to the transverse axis i.e. a reverse angle of about 5 degrees. In some embodiments, the leading flank edge is greater than the trailing edge angle by about 20 degrees.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a surgical system including one or more spinal implants, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-5, there are illustrated components of a spinal implant system 10 including a spinal implant, such as, for example, a coupling member and a bone fastener.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a coupling member, such as, for example, a set screw 12 configured for engagement with a bone screw 100, as described herein. Set screw 12 includes a portion, such as, for example, a head 14 and a portion, such as, for example a shaft 16. Head 14 includes a tool engaging portion 18 configured to engage a surgical tool or instrument (not shown), as described herein. In some embodiments, portion 18 includes a hexagonal cross-section to facilitate engagement with a surgical tool or instrument. In some embodiments, head 14 may have alternative cross-sections, such as, for example, rectangular, polygonal, hexalobe, oval, or irregular. In some embodiments, portion 18 may have a cruciform, phillips, square, polygonal or star cross sectional configuration configured for disposal of a correspondingly shaped portion of a surgical tool or instrument. In some embodiments, head 14 includes a hollow breakoff setscrew and an internal drive mechanism for removal of the setscrew.

Figure 2:
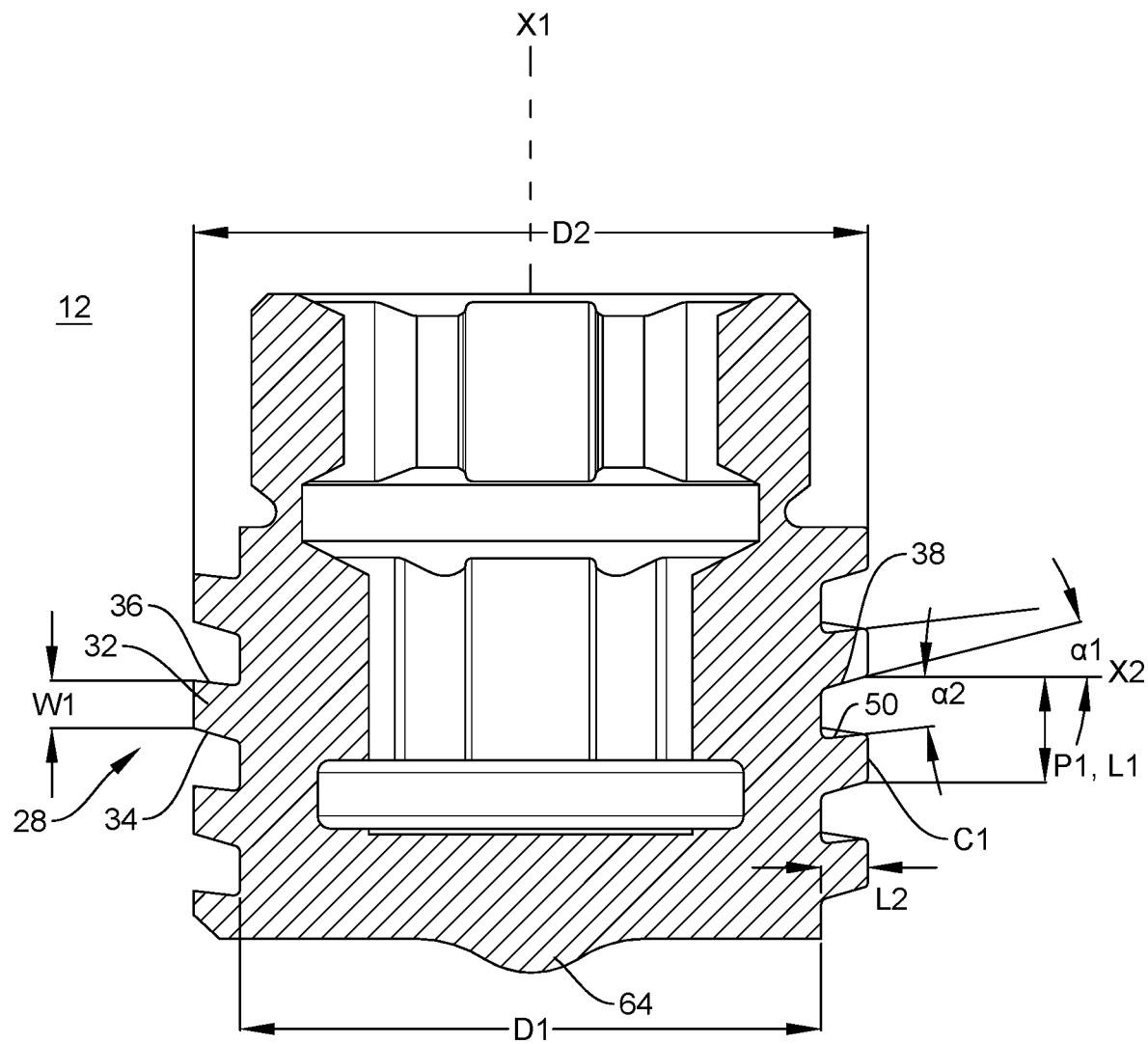
FIG. 2 is a cross section view of the components shown in FIG. 1.

Shaft 16 extends between an end 20 and an end 22, and defines an axis X1, as shown in FIG. 1. An axis X2 extends transverse, such as, for example orthogonal, to axis X1, as shown in FIG. 2. In some embodiments, axis X2 may be alternatively oriented relative to axis X1, such as, for example, angular orientations such as acute or obtuse. Shaft 16 includes an outer surface 26. Surface 26 includes threads 28. In some embodiments, surface 26 includes one or a plurality of threads 28 configured to enhance fixation with a receiver 102, as described herein. In some embodiments, threads 28 are continuous along surface 26. In some embodiments, threads 28 may include a single thread turn or a plurality of discrete threads. In some embodiments, penetrating elements may be located on shaft 16, such as, for example, a nail configuration, barbs, expanding elements, raised elements, ribs, and/or spikes to facilitate engagement of shaft 16 with bone screw 100.

Figure 6:
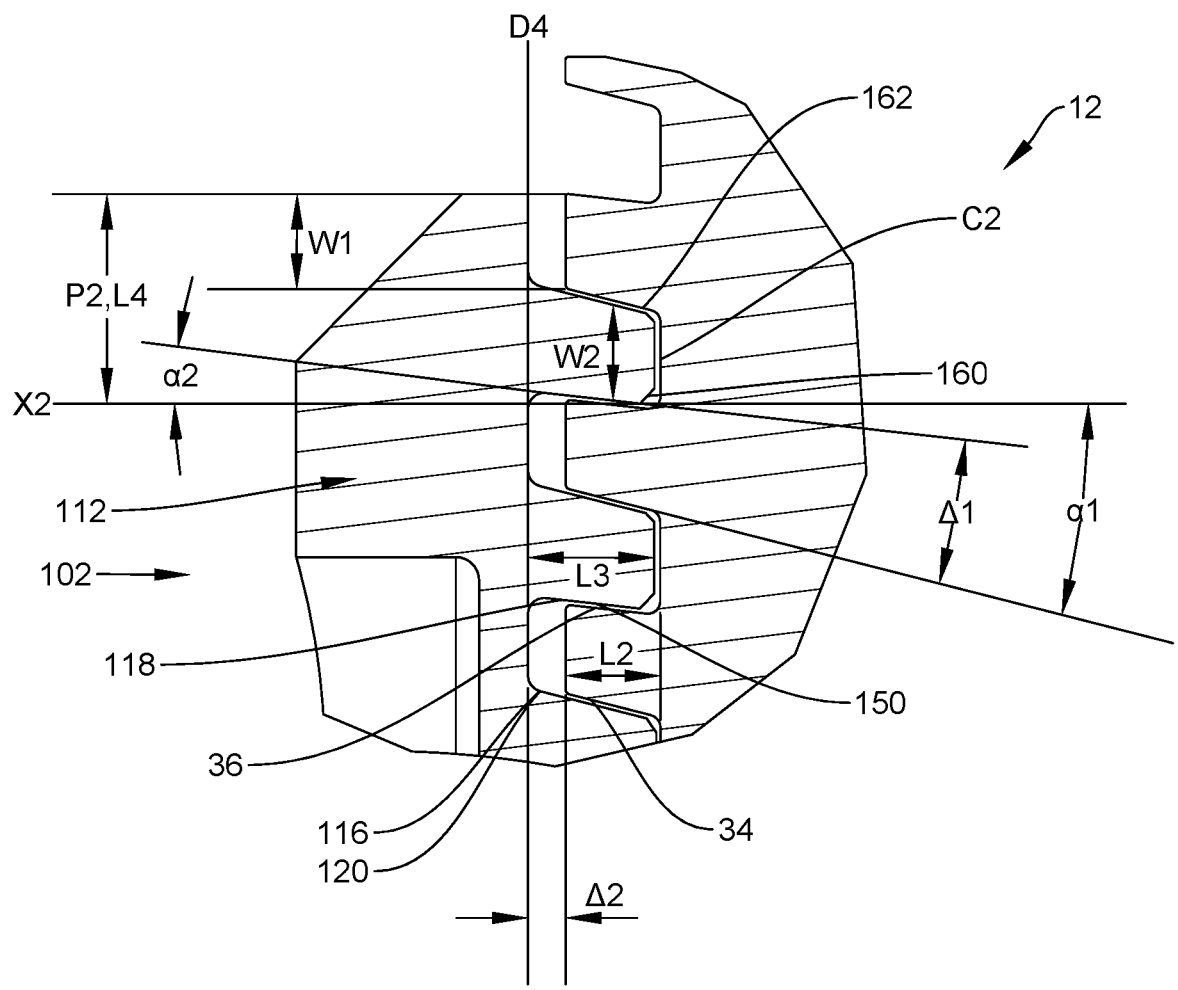
FIG. 6 is an exploded view of detail B shown in FIG. 5.

Threads 28 include a minor diameter D1 and a major diameter D2, as shown in FIG. 1. Threads 28 include an external thread form 32. External thread form 32 defines a shape of a contour of one complete thread 28. Thread form 32 includes a leading flank 34 and a trailing flank 36, as shown in FIG. 2. External thread form 32 is angled in a proximal and/or reverse angle orientation relative to axis X1, as shown in FIGS. 1, 2 and 6. For example, thread form 32 e.g., the leading and/or trailing flanks 34, 36 is angled toward end 20.

Leading flank 34 includes a surface 38 disposed at an angle $\alpha 1$ relative to axis X2, as shown in FIGS. 2 and 6. In some embodiments, angle $\alpha 1$ is about 15 degrees relative to axis X2. In some embodiments, surface 38 may be oriented in another manner relative to axis X2, such as, for example, by being perpendicular to axis X2 and/or having another angular orientations such as acute or obtuse relative to axis X2.

Trailing flank 36 includes a surface 50 disposed at an angle $\alpha 2$ relative to axis X2, as shown in FIGS. 2 and 6. In some embodiments, angle $\alpha 2$ is about −5 degrees relative to axis X2. In some embodiments, surface 50 may be alternatively oriented relative to axis X2, such as, for example, perpendicular and/or other angular orientations such as acute or obtuse.

In some embodiments, angle $\alpha 1$ differs is greater than from angle $\alpha 2$ by a difference $\Delta 1$, as shown in FIG. 6. In some of these embodiments, angle $\alpha 1$ is greater than angle $\alpha 2$ and, in contemplated others, angle $\alpha 1$ is less then angle $\alpha 2$. In some embodiments, for example, difference $\Delta 1$ is in a range of about 5 to about 20 degrees. In some embodiments, difference $\Delta 1$ is about 20 degrees.

Threads 28 define a pitch P1 having a length L1 extending between adjacent trailing flanks 36, as shown in FIG. 2. Leading flank 34 and trailing flank 36 merge at crest surface C1. In various embodiments, crest surface C1 extends along major diameter D2. Crest surface C1 includes a width W1 along major diameter D2. Width W1 is in various embodiments a percentage of length L1 of pitch P1. In some embodiments, width W1 is percentage of length L1 in a range of about 35 to about 50 percent of length L1. In some embodiments, width W1 is about 45 percent of length L1. The value for width W1 is selected to disperse a load applied by shear forces during engagement of set screw 12 with receiver 102. As such, width W1 is configured to resist and/or prevent effects of shear forces on set screw 12 and receiver 102 during tightening.

In some embodiments, width W1 bears a pre-determined relationship to pitch P1. In various embodiments, the relationship includes bone screw 100 being configured such that width W1 is a pre-set percentage of pitch P1, such as by width W1 being between about 40 and about 50 percent of pitch P1. In various embodiments, width W1 is any of between about 47 percent and about 43 percent of pitch P1, between about 46 and 44 percent of pitch P1, and about 45 percent of pitch P1.

Crest surface C1 is disposed at a length L2 from minor diameter D1, as shown in FIG. 2. In various embodiments, crest surface C1 includes a substantially planar configuration. In various embodiments, crest surface C1 is disposed parallel relative to axis X1. In some embodiments, crest surface C1 may be alternatively oriented relative to axis X1, such as, for example, transverse, and/or other angular orientations such as acute or obtuse.

Figure 4:
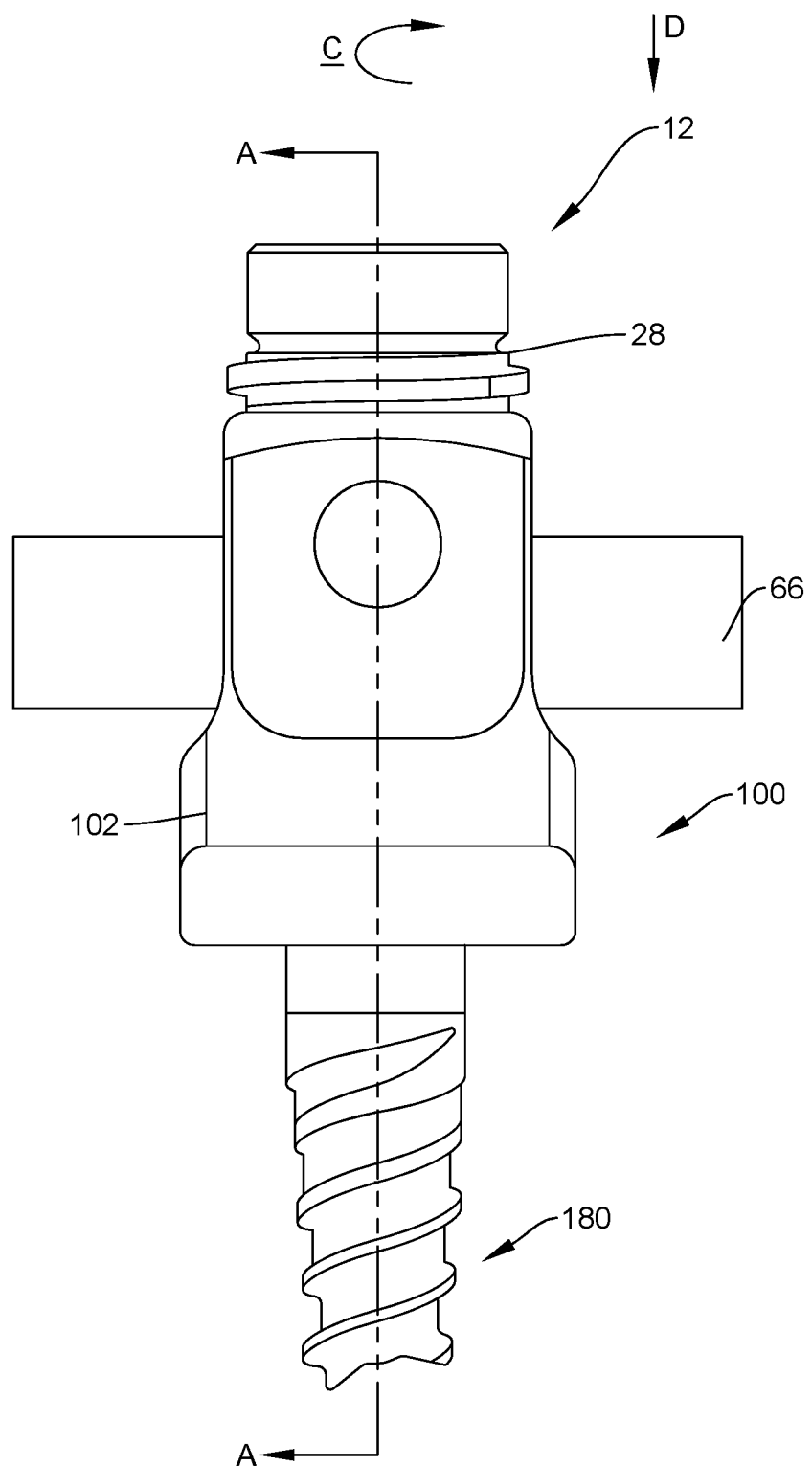
FIG. 4 is a side view of components of one embodiment of a surgical system in accordance with the principles of the present disclosure.
Figure 5:
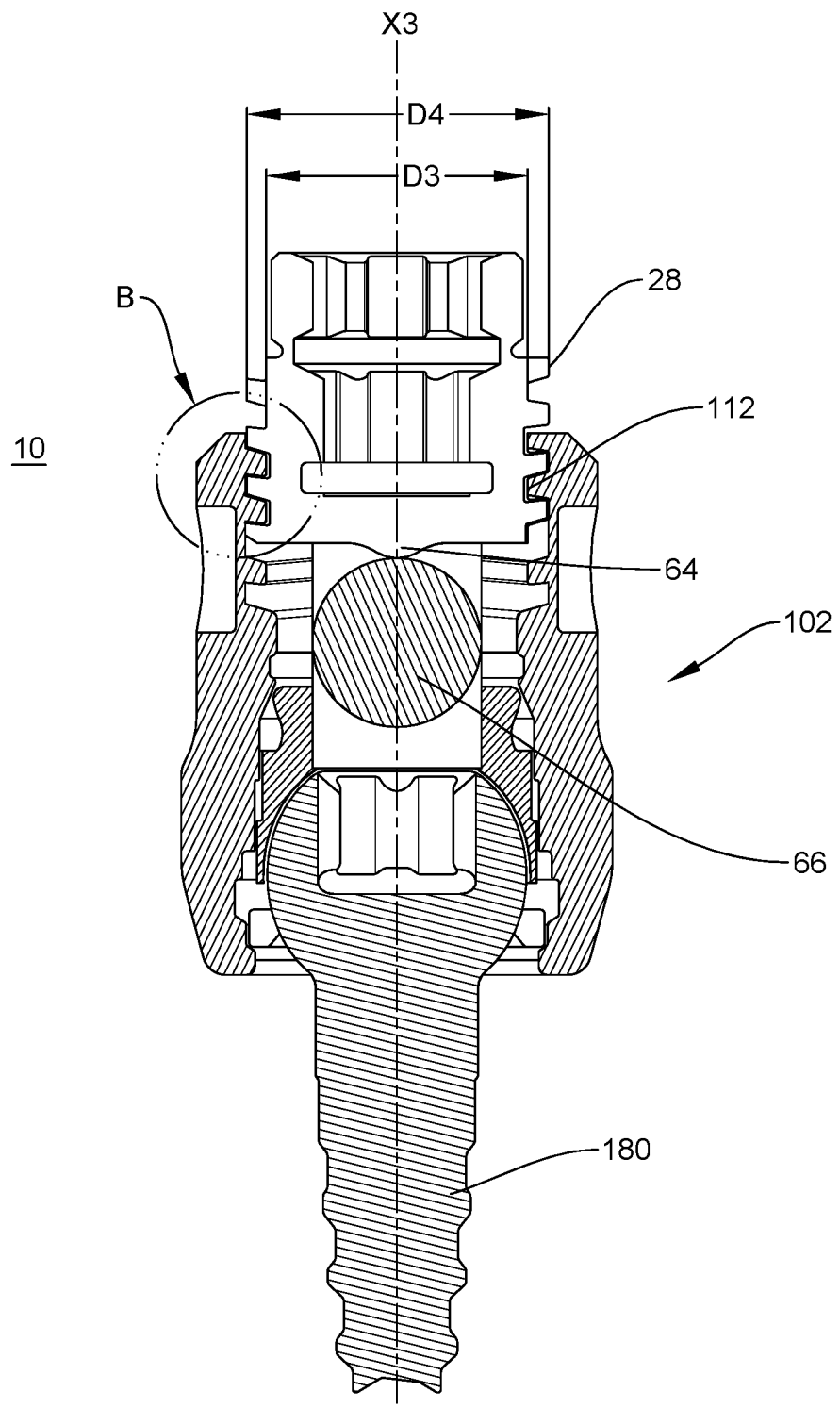
FIG. 5 is a cross section view taken along the lines A-A shown in FIG. 4.

End 20 and head 14 form a section, such as, for example, a neck 24 with head 14, as called out in FIG. 1 and shown also in FIGS. 2, 4, and 5. In some embodiments, end 20 includes a reduced diameter portion 60 at neck 24. In some embodiments, portion 60 is frangibly connected to head 14. In some embodiments, portion 60 is fabricated from a fracturing and/or frangible material such that manipulation of head 14 relative to shaft 16 can cause fracture at portion 60 to separate head 14 from shaft 16 at a predetermined force and/or torque limit, as described herein. In some embodiments, as force and/or torque is applied to head 14 and resistance increases, for example, due to fixation of shaft 16 within the receiver 102, as described herein, the predetermined torque and force limit is approached.

In some embodiments, head 14 can fracture from neck 24 and separate at a predetermined force or torque limit, which may be in a range of approximately 7 Newton meters (Nm) to approximately 12.5 Nm. In some embodiments, head 14 and/or shaft 16 may be fabricated from a homogenous material or heterogeneously fabricated from different materials, and/or alternately formed of a material having a greater degree, characteristic or attribute of plastic deformability, frangible property and/or break away quality to facilitate fracture and separation of head 14 from the shaft 16. In some embodiments, head 14 includes an inner diameter that facilitates a desired breakoff torque.

End 22 includes a surface 62 that includes a penetrating element 64 extending distally from surface 62. Element 64 is configured to engage a spinal implant, such as, for example, a spinal rod 66, as shown in FIGS. 4 and 5. Element 64 is configured to apply a force to spinal rod 66 to fix spinal rod with bone screw 100, as described herein.

Figure 3:
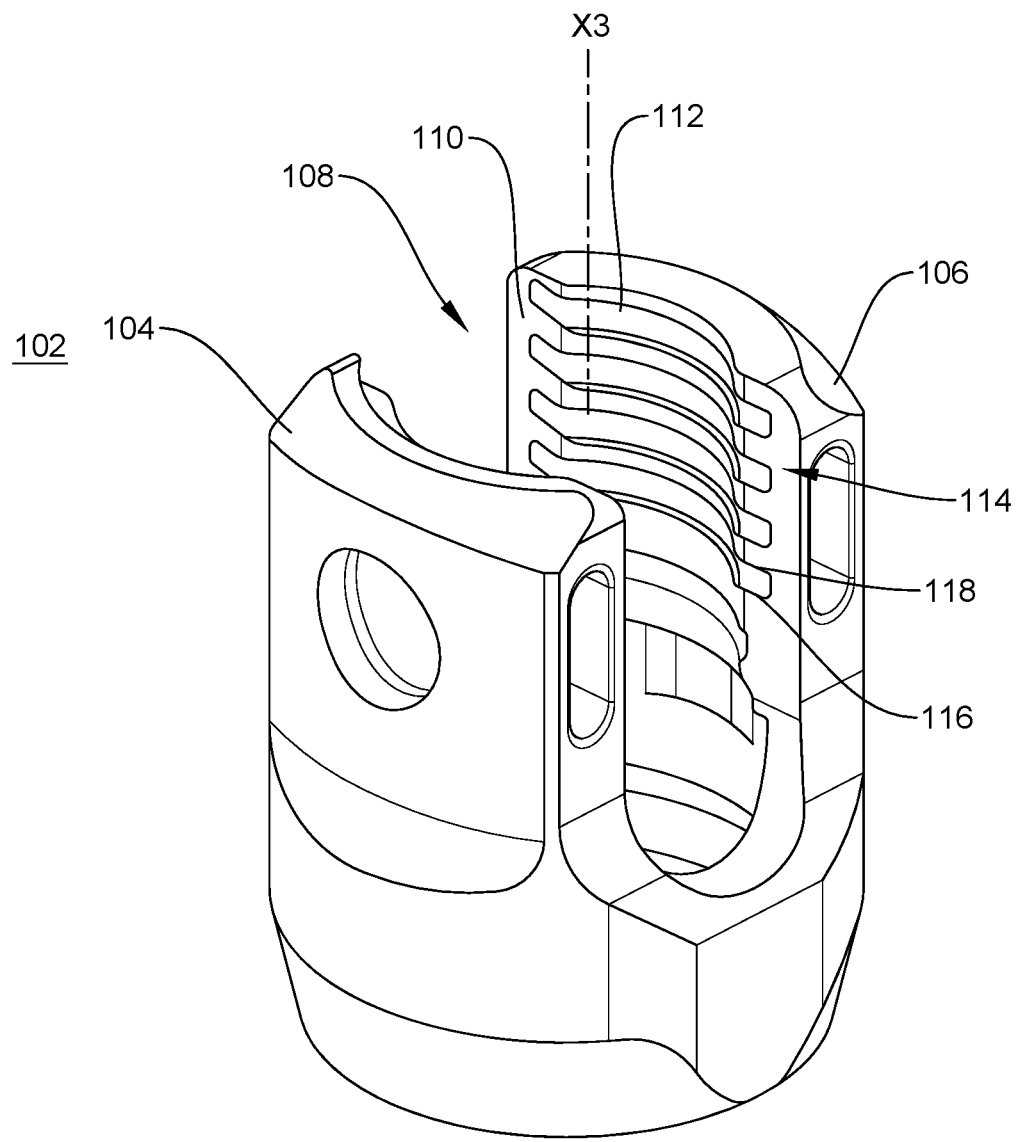
FIG. 3 is a perspective view of components of one embodiment of a surgical system in accordance with the principles of the present disclosure.

Bone screw 100 includes receiver 102, as shown in FIG. 3. Receiver 102 includes a pair of spaced apart arms 104, 106 that define an implant cavity 108 therebetween configured for disposal of spinal rod 66. Arms 104, 106 each extend parallel to an axis X3. In some embodiments, arms 104, 106 may be disposed at alternative orientations, relative to axis X3, such as, for example, transverse, perpendicular and/or other angular orientations such as acute or obtuse, coaxial and/or may be offset or staggered.

Cavity 108 is in various embodiments substantially U-shaped. In some embodiments, all or only a portion of cavity 108 may have alternative cross section configurations, such as, for example, closed, V-shaped, W-shaped, oval, oblong triangular, square, polygonal, irregular, uniform, non-uniform, offset, staggered, and/or tapered.

Receiver 102 includes an inner surface 110, as shown in FIG. 3. Surface 110 includes threads 112. Threads 112 include a minor diameter D3 and a major diameter D4, as shown in FIG. 5. Threads 112 include an internal thread form 114. Internal thread form 114 defines a shape of a contour of one complete thread 112. Internal thread form 114 is angled in a distal orientation relative to axis X3, as shown in FIG. 4. For example, internal thread form 114 is angled toward a distal end of receiver 102.

Internal thread form 114 includes a flank 116 and a flank 118, as shown in FIG. 6. Threads 112 define pitch P2 having a length L4 extending between adjacent flanks 118, as shown in FIG. 6. In some embodiments, pitch P1 (FIG. 2) is approximately equal to pitch P2. In some embodiments, pitch P1 is greater than pitch P2. In some embodiments, pitch P1 is less that pitch P2.

Flank 116 includes a surface 120 that extends transverse to axis X3. Surface 120 is disposed in an orientation to facilitate engagement with leading flank 34 for interlocking set screw 12 with receiver 102. In some embodiments, surface 120 may be alternatively oriented relative to axis X3, such as, for example, perpendicular and/or other angular orientations such as acute or obtuse.

Flank 118 includes a surface 150 that extends transverse to axis X3. Surface 150 is disposed in an orientation to facilitate engagement with trailing flank 36 for interlocking set screw 12 with receiver 102. In some embodiments, surface 150 may be alternatively oriented relative to axis X3, such as, for example, perpendicular and/or other angular orientations such as acute or obtuse.

Crest C2 extends between flank 116 and flank 118 and extends along minor diameter D3. Crest surface C2 includes a width W2 along minor diameter D3. Width W2 is a percentage of length L4 of pitch P2. In some embodiments, width W2 is a percentage of length L1 in a range of about 35 to about 50 percent of length L4. In some embodiments, width W2 is about 45 percent of length L4. Width W2 is configured to disperse a load applied by shear forces during engagement of set screw 12 with receiver 102. As such, engagement of set screw 12 with receiver 102 is configured to resist and/or prevent effects of shear forces on set screw 12 and receiver 102 during tightening.

In some embodiments, width W2 bears a pre-determined relationship to pitch P2. In various embodiments, the relationship includes bone screw 100 being configured such that width W2 is a pre-set percentage of pitch P2, such as by width W2 being between about 40 and about 50 percent of pitch P2. In various embodiments, width W2 is any of between about 47 percent and about 43 percent of pitch P2, between about 46 and 44 percent of pitch P1, and about 45 percent of pitch P2.

Crest surface C2 is disposed at a length L3 from major diameter D4, as shown in FIG. 6. In some embodiments, distance L3 is greater than distance L2 by a difference Δ2. The components are configured such that the difference Δ2 is sufficient to provide clearance between crest surface C1 and a surface defining major diameter D4, as shown in FIG. 6. The clearance between crest surface C1 and major diameter D4 facilitates expansion of threads 28 during engagement of set screw 12 with receiver 102. The space between crest surface C1 the surface defining major diameter D4 is configured to resist and/or prevent set screw 12 splaying arms 104, 106 during engagement of set screw 12 with receiver 102.

In various embodiments, flank 116 merges with crest surface C2 at a surface 160. Surface 160 can include an arcuate configuration relative to minor diameter D3, such that surface 160 is rounded.

Flank 118 merges with crest surface C2 at a surface 162. Surface 162 includes an arcuate configuration relative to minor diameter D3, such that surface 162 is rounded. In some embodiments, one or both of surfaces 160, 162 includes an arcuate configuration.

The arcuate configuration of surfaces 160, 162 prevent to surfaces 160, 162 from cutting into setscrew 12. For example, as set screw 12 is engaged with receiver 102, surfaces 160, 162 are load bearing surfaces. The arcuate configuration of surfaces 160, 162 resists and/or prevents surfaces 160, 162 from cutting into setscrew 12 when the load is applied. In some embodiments, this configuration is especially beneficial when receiver 102 includes a harder material than set screw 12.

Bone screw 100 includes a shaft 180, as shown in FIGS. 4 and 5. shaft 180 is configured for fixation with tissue of a patient (not shown). In some embodiments, shaft 180 has a cylindrical cross-section configuration and includes an outer surface having threads that define an external thread form. In some embodiments, the threads may include a single thread turn or a plurality of discrete threads. In some embodiments, engaging structures may be located on shaft 180, such as, for example, a nail configuration, barbs, expanding elements, raised elements and/or spikes to facilitate engagement of shaft 180 with tissue, such as, for example, vertebrae.

In some embodiments, all or only a portion of shaft 180 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 180 may have alternate surface configurations to enhance fixation with tissue such as, for example, rough, arcuate, undulating, mesh, porous, semi-porous, dimpled and/or textured. In some embodiments, all or only a portion of shaft 180 may be disposed at alternate orientations, relative to axis X4, such as, for example, transverse, perpendicular and/or other angular orientations such as acute or obtuse, co-axial and/or may be offset or staggered. In some embodiments, all or only a portion of shaft 180 may be cannulated.

In some embodiments, one or more of bone screws 100 and/or bone fasteners, as described herein, may include, for example, multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In assembly, operation and use, spinal implant system 10, similar to the systems and methods described herein, includes set screw 12 and bone screw 100, as described herein, and is employed with a surgical procedure for treatment of a spinal disorder affecting a section of a spine of a patient, as discussed herein. In some embodiments, the components of spinal implant system 10 may be employed with one or a plurality of vertebral levels of a spine. In some embodiments, the components of spinal implant system 10 may include one or a plurality of bone fasteners, spinal rods, plates, connectors and/or interbody devices.

In use, to treat the affected section of the spine, a medical practitioner obtains access to a surgical site in any appropriate manner, such as through incision and retraction of tissues. In some embodiments, the components of spinal implant system 10 may be used in any existing surgical method or technique including open surgery, mini-open surgery, and minimally invasive surgery including percutaneous surgical implantation. Once access to a surgical site(s) is obtained, the particular surgical procedure is performed for treating the spinal disorder. The components of spinal implant system 10 including set screw 12 and bone screw 100 are employed to augment the surgical treatment. The components of spinal implant system 10, as described herein, are delivered or implanted as a pre-assembled device or can be assembled in situ. The components of spinal implant system 10 may be completely or partially revised, removed or replaced. For example, shaft 180 is fastened with tissue, such as, for example, vertebrae, such that spinal rod 66 is disposed with receiver 102 for attachment with the vertebrae.

Set screw 12 is coupled with bone screw 100 adjacent a top surface of receiver 102. Set screw 12 is rotated in a clockwise direction, in a direction shown by arrow C in FIG. 4, via a surgical instrument or tool and translated, in a direction shown by arrow D in FIG. 4, such that threads 28 mate with threads 112 to couple set screw 12 with bone screw 100. As such, external thread form 32 simultaneously mates with internal thread form 114.

Translation of set screw 12 causes element 64 to engage spinal rod 66 such that set screw 12 provides a closure mechanism to dispose spinal rod 66 with cavity 108 and fix spinal rod 66 with receiver 102, and attach spinal rod 66 with the vertebrae. Width W1 at crest surface C1 and width W2 at crest surface C2 disperse the load applied by shear forces during engagement of set screw 12 with receiver 102. As such, widths W1, W2 are configured to resist and/or prevent effects of shear forces on set screw 12 and receiver 102 during tightening. Arcuate surfaces 160, 162 resist and/or prevent threads 112 from cutting and/or biting into the surface of setscrew 12 during engagement with receiver 102.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A coupling member comprising:
a shaft defining an axis and including at least one thread having an external thread form, the external thread form having a leading flank and a trailing flank, the external thread form defining a pitch and a crest, the crest having a width in a range of about 35% to about 50% of the pitch of the external thread form,
wherein the leading flank and the trailing flank are angled in a proximal orientation relative to the thread axis,
wherein the external thread form is configured to interlock with an internal thread form of an implant receiver,
wherein the leading flank is disposed at a first angle relative to a transverse axis of the at least one thread and the trailing flank is disposed at a second angle relative to the transverse axis, and
wherein the first angle is about 15 degrees relative to the transverse axis and the second angle is about −5 degrees relative to the transverse axis.

2. The coupling member recited in claim 1, wherein the width is about 45% of the pitch of the external thread form.

3. The coupling member recited in claim 1, wherein the external thread form includes a crest surface disposed in a generally parallel orientation relative to the transverse axis.

4. The coupling member recited in claim 1, wherein the external thread form includes a crest surface having a substantially planar configuration.

5. The coupling member recited in claim 1, wherein the at least one thread includes a plurality of threads disposed along the shaft.

6. The coupling member recited in claim 1, wherein the implant receiver includes at least one thread having the internal thread form, the at least one thread including at least one rounded corner.

7. The coupling member recited in claim 1, wherein the thread of the implant receiver includes a crest having a width in a range of about 35% to about 50% of a pitch of the internal thread form.

8. The coupling member recited in claim 1, wherein the implant receiver includes spaced-apart walls, each wall comprising a thread having the internal thread form, each thread comprising a pair of rounded corners.

9. The coupling member recited in claim 1, further comprising a head coupled to the shaft, the head including a proximal surface and the shaft including a distal surface opposite the proximal surface, the shaft comprising a penetrating element extending distally from the distal surface.

10. The coupling member recited in claim 1, further comprising a head coupled to the shaft, the head being frangibly coupled to the head at a reduced diameter portion of the coupling member.

11. The coupling member recited in claim 1, further comprising a head coupled to the shaft, the coupling member comprising a tool socket extending through the head and into the shaft, the tool socket having a first portion, a second portion and a third portion, the second portion being positioned between the first portion and the third portion, the first portion and the third portion each having a hexagonal cross-section, the second portion having a circular cross-section.

12. A spinal implant comprising:
an implant receiver including at least one thread defining an internal thread form having at least one rounded corner; and
a coupling member including at least one thread defining a thread axis, and an external thread form having a leading flank and a trailing flank, the leading flank and the trailing flank are angled in a proximal orientation relative to the thread axis, the external thread form defines a crest having a width in a range of about 35-50% of a pitch of the external thread form,
the leading flank being disposed at a first angle relative to a transverse axis of the at least one thread and the trailing flank being disposed at a second angle relative to the transverse axis, the first angle being about 15 degrees relative to the transverse axis and the second angle being about −5 degrees relative to the transverse axis,
the external thread form being configured to interlock with the internal thread form.

13. The spinal implant recited in claim 12, wherein the implant receiver includes spaced apart walls, each wall including a thread having the internal thread form, each thread including a pair of rounded corners.

14. The spinal implant recited in claim 12, wherein the first angle is about 20 degrees greater than the second angle.

15. The spinal implant recited in claim 12, wherein the width is 45% of a pitch of the external thread form.

16. The spinal implant recited in claim 12, wherein:
the internal thread form has a major diameter and includes a crest disposed at a first length from the major diameter, the external thread form having a minor diameter, the leading flank and the trailing flank merging at a crest, the crest of the external thread form being disposed at a second length from the minor diameter, the first length being greater than the second length, and
wherein the external thread form is configured to interlock with the internal thread form such that the crest of the external thread form is spaced apart from a surface of the implant receiver that defines the major diameter.

17. The spinal implant recited in claim 12, wherein the internal thread form includes a leading flank and trailing flank merging at a crest of the internal thread form, the internal thread form being rounded between the leading flank of the internal thread form.

18. A spinal implant system comprising:
at least one bone screw including an implant receiver and a tissue penetrating shaft, the implant receiver including at least one thread defining an internal thread form having at least one rounded corner;
a set screw including at least one thread defining a thread axis, and an external thread form having a leading flank and a trailing flank, the leading flank and the trailing flank are angled in a proximal orientation relative to the thread axis, the external thread form defines a crest having a width in a range of about 35-50% of a pitch of the external thread form, the leading flank being disposed at a first angle relative to a transverse axis of the at least one thread and the trailing flank being disposed at a second angle relative to the transverse axis, the first angle being about 15 degrees relative to the transverse axis and the second angle being about −5 degrees relative to the transverse axis,
the external thread form being configured to interlock with the internal thread form; and
a spinal rod configured for disposal with the implant receiver and engagement with the set screw.

19. The spinal implant system recited in claim 18, wherein the width is 45% of a pitch of the external thread form.

\* \* \* \* \*